United States Patent [19]

Adolphi et al.

[11] B 4,013,740
[45] Mar. 22, 1977

[54] SUBSTITUTED FLUOROPHOSPHAZENES

[75] Inventors: Heinrich Adolphi, Limburgerhof; Gerd Wunsch, Speyer; Volker Kiener, Ludwigshafen, all of Germany

[73] Assignee: BASF Aktiengesellschaft, Ludwigshafen (Rhine), Germany

[22] Filed: July 1, 1974

[21] Appl. No.: 484,437

[44] Published under the second Trial Voluntary Protest Program on March 30, 1976 as document No. B 484,437.

[30] Foreign Application Priority Data

July 10, 1973 Germany .......................... 2334917

[52] U.S. Cl. ..................... 260/927 N; 260/455 P; 260/482 C; 260/543 PN; 424/209

[51] Int. Cl.$^2$ ...................... C07C 9/15; A01N 9/36
[58] Field of Search ................................. 260/927 N

[56] References Cited
UNITED STATES PATENTS 2,214,769   9/1940   Lipkin ........................... 260/927 N

*Primary Examiner*—Anton H. Sutto
*Attorney, Agent, or Firm*—Johnston, Keil, Thompson & Shurtleff

[57] ABSTRACT

New and valuable substituted fluorophosphazenes, pesticides containing these compounds, and a process for controlling pests with these compounds.

11 Claims, No Drawings

SUBSTITUTED FLUOROPHOSPHAZENES

This application discloses and claims subject matter described in German Pat. Application No. P 23 34 917.9, filed July 10, 1973, which is incorporated herein by reference.

The present invention relates to new and valuable substituted fluorophosphazenes, a process for controlling pests with these compounds, and pesticides containing these compounds as active ingredients.

We have found that substituted fluorophosphazenes of the formula

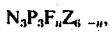

where Z denotes OR, OT, SR, SY, NHNHR, NHCSR,

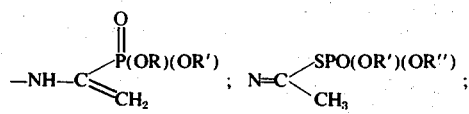

NHCOXR or NHCONR$_2$, R, R' and R'' denoting alkyl or aryl, X denoting oxygen or sulfur, T denoting alkyl and Y denoting alkyl of more than 2 carbon atoms, and $n$ denotes one of the integers 2, 3, 4 and 5, $n$ being 4 or 5 when Z is NHNHR, $n$ being 2, 3 or 4 when Z is OR, $n$ being 2, 3 or 4 when Z is SR, and $n$ otherwise being 5, are excellently suited for controlling pests.

The active ingredients are generally prepared from cyclic phosphorus nitride fluorides. To obtain compounds of the formulas N$_3$P$_3$F$_n$(OR)$_{6-n}$ or N$_3$P$_3$F$_n$(SR)$_{6-n}$, the esters and thioesters of the fluorophosphazenes, a solution of the phosphorus nitride fluoride is generally reacted in a solvent, e.g., ether, THF (tetrahydrofuran), benzene, toluene, chlorobenzene and alcohol, with the calculated amount of alcoholate or mercaptide, e.g., in the form of the sodium salt. The reaction is generally carried out at temperatures of from −20° to +100°C, preferably from 0° to 90°C. The fluorophosphazenes prepared in this manner are usually colorless liquid compounds which can generally be purified by distillation.

The reaction of NaSCH$_3$ with N$_3$P$_3$F$_6$ to give N$_3$P$_3$F$_4$(SCH$_3$)$_2$ proceeds in accordance with the equation N$_3$P$_3$F$_6$ + 2 NaSCH$_3$ ⟶ N$_3$P$_3$F$_4$(SCH$_3$)$_2$ + 2 NaF.

The fluorophosphazene hydrazine derivatives N$_3$P$_3$F$_n$(NHNHR)$_{6-n}$ are obtained by reacting the fluorophosphazene in a solvent, e.g., ether, THF, benzene and chlorobenzene, with the calculated amount of the hydrazine.

The reaction is generally carried out at temperatures of from −40° to +140°C, preferably 0° to 100°C, in the presence or absence of acid-binding agents. Particularly preferred as such are tertiary amines or heterocyclic amines, e.g., pyridine. However, a 100% excess of the primary or secondary amine may also be used as acid acceptor, e.g., in accordance with the equation N$_3$P$_3$F$_6$ + 2 H$_2$NNHCH$_3$ ⟶ N$_3$P$_3$F$_5$NHNHCH$_3$ + H$_2$NNHCH$_3$ · HF.

The fluorophosphazene acid amide derivatives are obtained as follows. If fluorophosphazenimine chloride,

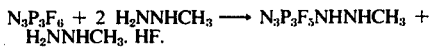

is reacted with a thiocarboxamide, the corresponding fluorophosphazene thioacid amide derivative is obtained in almost quantitative yield. With thioacetamide the reaction proceeds in accordance with the following equation:

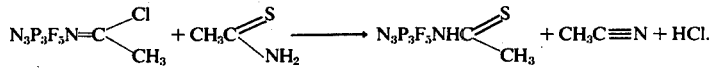

The reaction may be carried out in a solvent, e.g., ether, THF and benzene, at atmospheric or superatmospheric pressure and at temperatures of from 10° to 100°C.

The compounds

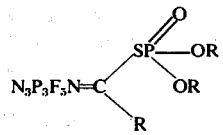

are obtained starting from the from the appropriate fluorophosphazenimine chloride

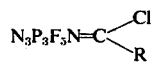

by reaction with a salt (preferably sodium) of a thiophosphoric acid ester, e.g., NaSP(O)(OR)$_2$.

Solvents, e.g., ether, THF, benzene, toluene and chloroform, are generally used in the reaction.

The reaction is best carried out at a temperature of from −10° to +110°C.

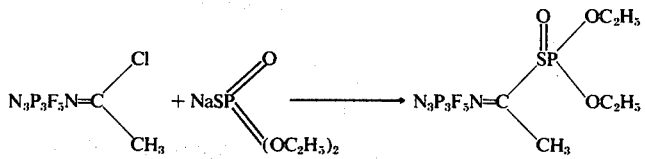

If the phosphazenimine chloride is reacted with a phosphite as in an Arbusov reaction, it is not the expected imine compound which is formed with the elimination of methyl chloride but the N-fluorophosphazeno-α-dimethoxyphosphonylenamine.

With trimethyl phosphite the reaction proceeds according to the following equation:

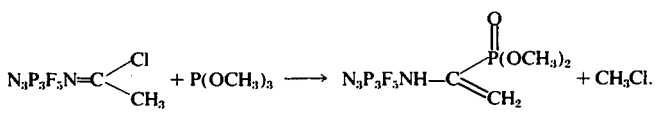

The reaction may be carried out in the presence or absence of a solvent, e.g., ether, THF, chlorinated hydrocarbons (CHCl$_3$, CH$_2$Cl) and aromatic hydrocarbons (benzene, toluene). The temperature is generally from 10° to 150°C.

Previous attempts to prepare fluorophosphazene isocyanate, N$_3$P$_3$F$_5$NCO, by reaction of N$_3$P$_3$F$_5$NSO with oxalyl chloride only resulted in yields of 8%, Z. Naturforsch. (H.W. Roesky, E. Janssen), 26b, 679 et seq., 1971.

We have now found that N$_3$P$_3$F$_5$NCO may be prepared in surprisingly high yields by converting the N-sulfynylamine group NSO on the N$_3$P$_3$F$_5$ radical to the isocyanate group with COCl$_2$. It is preferred first to place N$_3$P$_3$F$_5$NSO in a solvent, generally one boiling at above 110°C, e.g., chlorobenzene and tetrachloroethane, and then to pass in phosgene at a temperature of from 20° to 100°C, preferably 70° to 100°C. An excess of phosgene is not detrimental.

The reaction may be accelerated by adding catalytic amounts of pyridine, preferably from 0.01 to 1 ml per 100 g of N$_3$P$_3$F$_5$NSO.

For working up, first the SOCl$_2$ and subsequently the N$_3$P$_3$F$_5$NCO are distilled off.

$$N_3P_3F_5NSO + COCl_2 \rightarrow N_3P_3F_5NCO + SOCl_2$$

The fluorophosphazene isocyanate which may be readily prepared in large amounts in this way is very reactive and may be used as an intermediate for a variety of products.

Aliphatic and aromatic amines give the corresponding urea derivatives. What is remarkable is that the ring itself is not attacked by an excess of amine, e.g.:

$$N_3P_3F_5NCO + NHR_2 \rightarrow N_3P_3F_5NHCONR_2,$$

R denoting alkyl or aryl.

Phosphates containing the carbamate or thiocarbamate radical as substituent are formed with alcohols and thioalcohols:

$$N_3P_3F_5NCO + HOC_2H_5 \rightarrow N_3P_3F_5NHCOOC_2H_5.$$

Some of the derivatives of isocyanate fluorophosphazenes are distillable liquids, others crystallizable substances, and they are stable to hydrolysis. They are preferably prepared in solvents, e.g., ether, THF, benzene, toluene, and chloroform, and at temperatures of from −10° to +120°C.

EXAMPLE 1

Preparation of N$_3$P$_3$F$_5$(SCH$_3$)$_2$

At −20°C and while stirring, a slurry of 56 parts (by weight) of NaSCH$_3$ in 300 parts of ether is added to a solution of 100 parts of N$_3$P$_3$F$_6$ in 400 parts of ether. After 30 minutes the reaction is brought to the reflux temperature and boiled at this temperature for 4 hours. Subsequently, the NaF is removed by filtration. The compound is purified by fractional distillation.

Yield: 66 parts = 54% of theory, with reference to N$_3$P$_3$F$_6$; b.p. (3 mm): 49° to 53°C.

EXAMPLE 2

Preparation of N$_3$P$_3$F$_2$(OCH$_3$)$_4$

In a manner similar to that described in Example 1 a slurry of 86 parts of NaOCH$_3$ in 400 parts of ether is added, at −60°C and while stirring, to 100 parts of N$_3$P$_3$F$_6$ in 200 parts of ether. After the temperature of the reaction mixture has risen to +20°C, it is boiled under reflux for 6 hours. Subsequently, the NaF is filtered off. The compound is purified by fractional distillation. Yield: 59 parts = 49% of theory; b.p. (0.1 mm): 52° to 54°C.

The following compounds may be prepared in the same manner as in Example 1:

|  | b.p. (mm) | °C |
| --- | --- | --- |
| N$_3$P$_3$F$_3$(SCH$_3$)$_3$ | 0.1 | 80 |
| N$_3$P$_3$F$_4$(OCH$_3$)$_2$ | 67 | 93 |
| N$_3$P$_3$F$_3$(OCH$_3$)$_3$ | 0.01 | 45 to 47 |
| N$_3$P$_3$F$_4$(OC$_2$H$_5$)$_2$ | 0.01 | 33 to 35 |
| N$_3$P$_3$F$_3$(OC$_2$H$_5$)$_3$ | 0.01 | 59 to 62 |
| N$_3$P$_3$F$_2$(OC$_2$H$_5$)$_4$ | 0.01 | 137 |
| N$_3$P$_3$F$_4$(OCH$_2$CH$_2$CH$_3$)$_2$ | 0.01 | 43 |
| N$_3$P$_3$F$_2$(OCH$_2$CH$_2$CH$_3$)$_4$ | 0.01 | 90 to 95 |

EXAMPLE 3

Preparation of N$_3$P$_3$F$_5$NHNHCH$_3$

At −10°C, 18.4 parts of H$_2$NNHCH$_3$ in 50 parts of ether is slowly dripped into a solution of 50 parts of N$_3$P$_3$F$_6$ in 200 parts of ether. The mixture is heated to 25°C and stirred at this temperature for 2 hours. Subsequently, the HF.H$_2$NNHCH$_3$ is filtered off, the filtrate is concentrated and the residue fractionally distilled at 6 mm. The fraction distilling between 63° and 72°C (mainly N$_3$P$_3$F$_5$NHNHCH$_3$) is recrystallized from hexane.

Yield: 46.4 parts = 84% of theory, with reference to N$_3$P$_3$F$_6$; m.p.: 80°C.

The following compound is prepared in the same manner: N$_3$P$_3$F$_5$NHN(CH$_3$)$_2$ b.p. (35 mm): 83° to 85°C

EXAMPLE 4

Preparation of

At room temperature, 50 parts of

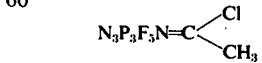

is dripped into 12.3 parts of

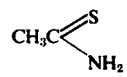

in 150 parts of ether, and the mixture stirred for 4 hours at this temperature. The mixture is subsequently concentrated and the residue recrystallized from heptane.

Yield: 35.1 parts = 71% of theory, with reference to

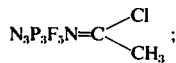

m.p.: 89°C.

EXAMPLE 5

Preparation of

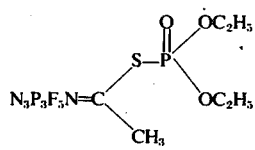

At room temperature, 50 parts of

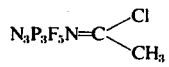

is dripped into 36 parts of $NH_4SP(O)(OC_2H_5)_2$ in 100 parts of benzene. A precipitate forms immediately. The mixture is stirred for 4 hours at 40°C and subsequently filtered. The filtrate is concentrated, the residue is taken up in hexane and filtered through activated carbon, and the hexane is filtered at 50°C in a water-jet vacuum. There remains 43 parts (56% of theory) of a pale yellow, undistillable oil which according to ultimate analysis and infrared spectra has the composition

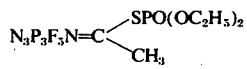

EXAMPLE 6

Preparation of

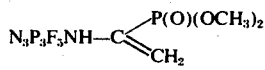

30 parts of $P(OCH_3)_3$ in 50 parts of benzene is added to 50 parts of

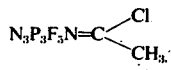

in 300 parts of benzene. The mixture is subsequently boiled under reflux for 90 minutes. The benzene and excess phosphite are distilled off and the residue is fractionally distilled at 0.01 mm.

Yield: 57 parts = 92% of theory; b.p. (0.01 mm): 100°C.

The following compounds are prepared in the same manner as in Example 6:

|  | b.p. (mm) | °C | m.p. °C |
|---|---|---|---|
| $N_3P_3F_5NH$—C(=O)P(OC_2H_5)_2 CH_2 | 0.01 | 105 | 58 to 59 |
| $N_3P_3F_5NH$—C(=O)P(OCH_3)_2 CH—CH_3 | 0.01 | 113 to 115 |  |

EXAMPLE 7

Preparation of $N_3P_3F_5NCO$ 0.25 part of pyridine is added to 100 parts of $N_3P_3F_5NSO$ in 300 parts of chlorobenzene. At 95°C, 40 parts of phosgene is passed in over a period of 2 hours. The $SOCl_2$ which has formed is distilled off, and subsequently $N_3P_3F_5NCO$.

Yield: 65 parts = 85% of theory; b.p. (760 mm): 100°C.

EXAMPLE 8

Preparation of $N_3P_3F_5NHCOOCH_3$ 8.1 parts of $CH_3OH$ is added to 50 parts of $N_3P_3F_5NCO$ in 150 parts of ether, and the mixture boiled under reflux for 2 hours. The solvent is then distilled off and the residue recrystallized from hexane.

47 parts (87% of theory) of white crystals of the desired compound is obtained; m.p.: 72° to 73°C.

The following compounds were obtained in the same manner as in Example 8:

|  | b.p. (mm) | °C | m.p. °C |
|---|---|---|---|
| $N_3P_3F_5NHCOOC_2H_5$ | 0.1 | 41 | — |
| $N_3P_3F_5NHCOSC_2H_5$ | 0.01 | 99 | — |
| $N_3P_3F_5NHCON(C_2H_5)_2$ | — | — | 115 |

Application may be effected for instance in the form of directly sprayable solutions, powders, suspensions, dispersions, emulsions, oil dispersions, pastes, dusts or granules. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes, methanol, ethanol, propanol, butanol, chloroform, carbon tetrachloride, cyclohexanol, cyclohexanone, chlorobenzene, isophorone, etc., and strongly polar solvents such as dimethylformamide and dimethyl sulfoxide are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ehters, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules may be prepared by bonding the active ingredients to solid carriers. Examples of solid carriers are mineral earths such as silica gel, silicic acid, silicates, talc, kaolin, Attaclay, limestone, lime chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably from 0.5 to 90, % by weight of active ingredient.

There may be added to the compositions or individual active ingredients (if desired, immediately before use) oils of various types, herbicides, fungicides, nematocides, insecticides, bactericides and trace elements.

These agents may be added to the agents of the invention in a ratio by weight of from 1:10 to 10:1.

Examples of pests are termites, e.g., Reticulitermes sp., Macrotermes sp., Microtermes sp., and Kalotermes sp.; ligniperdous beatles, e.g., *Hylotrupes bajulus* (house longhorn), *Anobium punctatum*, and Lyctus sp.; flies, e.g., *Musca domestica*, *Fannia canicularis*, *Muscina stabulans*, and *Stomoxys calcitrans;* mosquitoes, e.g., Aedes sp., Culex sp., Anopheles sp. Phlebotomus sp., and Simulium sp.; cockroaches, e.g., Blatta sp., Blatella sp., and Periplaneta; butterflies, e.g., Spodoptera sp., Heliothis sp., Plutella sp., Earias sp., and Ephestia sp.; and fresh-water snails, e.g., Planorbis sp., and Australorbis sp.

The following active ingredients were used in the experiments:

1. 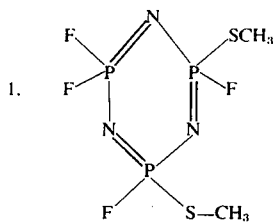

2. 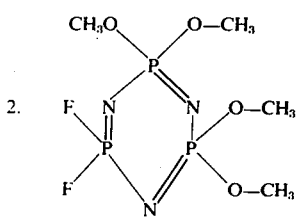

3. 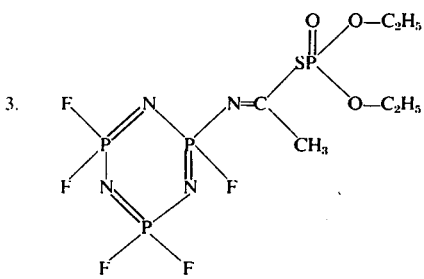

4. 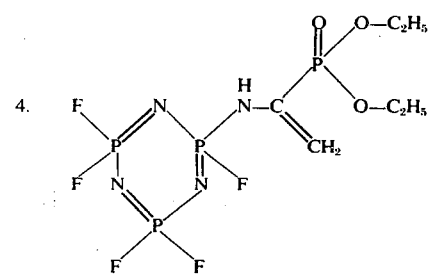

5. 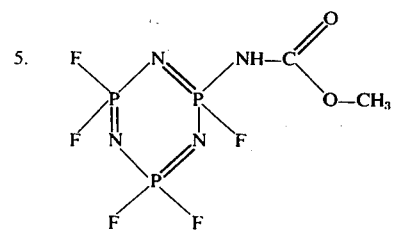

6. 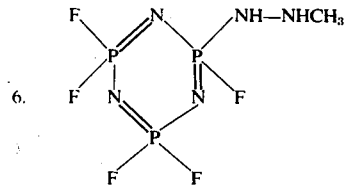

Comparative agents

I. Decachlorotetracyclodecanone (U.S. Pat. No. 2,616,825)

II. 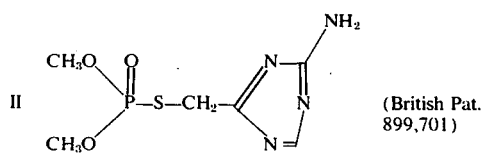 (British Pat. 899,701)

EXAMPLE 9

Contact action on oriental cockroach (*Blatta orientalis*)

1 liter beakers are wetted with acetonic solutions of the active ingredients. After evaporation of the solvent, cockroaches are placed in the beakers. The action is determined after 48 hours.

| Active ingredient | Amount of active ingredient | | Mortality |
|---|---|---|---|
| I | 10.0 | mg | 100% |
|  | 5.0 | mg | 20% |
| II | 5.0 | mg | 20% |
| 2 | 2.5 | mg | 100% |
| 3 | 0.2 | mg | 100% |
|  | 0.1 | mg | 80% |
| 4 | 0.5 | mg | 100% |
|  | 0.25 | mg | 80% |
| 5 | 0.25 | mg | 100% |

EXAMPLE 10

Contact action on houseflies (*Musca domestica*)

Petri dishes 10 cm in diameter are uniformly wetted with acetonic solutions of the active ingredients. After evaporation of the solvent, 20 4-day-old houseflies are placed in each dish and the mortality rate is determined after 4 hours.

| Active ingredient | Amount of active ingredient | | Mortality |
|---|---|---|---|
| I | 2.0 | mg | 40% |
| II | 2.0 | mg | 10% |
| 2 | 0.2 | mg | 80% |
| 3 | 0.02 | mg | 100% |
| 4 | 0.2 | mg | 100% |
| 5 | 0.2 | mg | 100% |

EXAMPLE 11

Action on larvae of the yellow fever mosquito (*Aedes aegypti*)

Larvae of the yellow fever mosquito in the 3rd and 4th development stage are placed in 100 ml of water to which aqueous emulsions of the active ingredients are added. The mortality rate is determined after 24 hours.

| Active ingredient | Amount of active ingredient | | Mortality |
|---|---|---|---|
| I | 5.0 | ppm | ineffective |
| 1 | 0.5 | ppm | 95% |
| 2 | 1.0 | ppm | 100% |
| 3 | 2.0 | ppm | 90% |
| 4 | 0.5 | ppm | 100% |
|  | 0.25 | ppm | 80% |
| 6 | 1.0 | ppm | 100% |

EXAMPLE 12

Contact action and effect of ingested food on caterpillars of the cabbage moth (*Plutella maculipennis*)

Young cabbage leaves are dipped for 5 seconds into aqueous emulsions of the active ingredients. After the layer has dried, caterpillars in the 4th and 5th larval stages are placed on the leaves. The action is assessed after 48 hours.

| Active ingredient | Amount of active ingredient | Mortality |
|---|---|---|
| I | 0.1% | 90% |
|  | 0.05% | 80% |
| 1 | 0.05% | 100% |
| 2 | 0.01% | 100% |
| 3 | 0.005% | 80% |
| 4 | 0.005% | 80% |
| 6 | 0.02% | 80% |

EXAMPLE 13

Action on freswater snails (*Planorbis*)

Aqueous emulsions of the active ingredients are added to 100 ml of water. Adult snails are used. The action is assessed after 48 hours.

| Active ingredient | Amount of active ingredient | | Mortality |
|---|---|---|---|
| I | 1.0 | ppm | 100% |
|  | 0.5 | ppm | 20% |
| 1 | 0.1 | ppm | 100% |
|  | 0.05 | ppm | 80% |
| 4 | 0.05 | ppm | 100% |
| 6 | 0.05 | ppm | 80% |

We claim:
1. A substituted fluorophosphazene of the formula

$$N_3P_3F_nZ_{6-n},$$

where Z denotes OR or SR, wherein R denotes lower alkyl and n denotes one of the integers 2, 3, or 4.

2. A compound as claimed in claim 1 wherein Z is OR.
3. A compound as claimed in claim 2 wherein R is —CH$_3$.
4. A compound as claimed in claim 2 wherein R is —CH$_3$ and n is 4.
5. A compound as claimed in claim 2 wherein R is —CH$_3$ and n is 3.
6. A compound as claimed in claim 2 wherein R is —C$_2$H$_5$ and n is 2, 3 or 4.
7. A compound as claimed in claim 2 wherein R is —CH$_2$CH$_2$CH$_3$ and n is 2.
8. A compound as claimed in claim 2 wherein R is —CH$_2$CH$_2$CH$_3$ and n is 4.
9. A compound as claimed in claim 1 wherein Z is —SCH$_3$ and n is 3.
10. A compound of the formula

[structure of cyclic phosphazene with F, SCH$_3$ substituents]

11. A compound of the formula

[structure of cyclic phosphazene with F, OCH$_3$ substituents]